(12) United States Patent
Sakai (10) Patent No.: US 9,179,830 B2
(45) Date of Patent: Nov. 10, 2015

(54) SCANNING ENDOSCOPE APPARATUS (71) Applicant: OLYMPUS MEDICAL SYSTEMS CORP., Tokyo (JP)

(72) Inventor: Yuji Sakai, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/245,086

(22) Filed: Apr. 4, 2014

(65) Prior Publication Data

US 2014/0296639 A1    Oct. 2, 2014

Related U.S. Application Data

(63) Continuation of application No. PCT/JP2013/075001, filed on Sep. 17, 2013.

(30) Foreign Application Priority Data

Oct. 11, 2012   (JP) ................. 2012-226227

(51) Int. Cl.
   *A61B 1/07*       (2006.01)
   *A61B 1/00*       (2006.01)
   *G02B 23/26*      (2006.01)
   *G02B 26/10*      (2006.01)
   *A61B 1/005*      (2006.01)
   *G02B 23/24*      (2006.01)
   *A61B 5/00*       (2006.01)

(52) U.S. Cl.
   CPC ................. *A61B 1/07* (2013.01); *A61B 1/0051* (2013.01); *A61B 1/00059* (2013.01); *A61B 1/00096* (2013.01); *A61B 1/00165* (2013.01); *A61B 1/00172* (2013.01); *A61B 1/00188* (2013.01); *G02B 23/2469* (2013.01); *G02B 23/2476* (2013.01); *G02B 23/26* (2013.01); *G02B 26/10* (2013.01); *A61B 1/0011* (2013.01); *A61B 1/00105* (2013.01); *A61B 5/0062* (2013.01)

(58) Field of Classification Search
   CPC ........... A61B 1/00172; A61B 1/00188; A61B 1/00163; A61B 1/00165; A61B 1/00096; A61B 1/07; A61B 5/0062; A61B 5/0064; A61B 5/0066; A61B 5/0068; G02B 23/2469
   See application file for complete search history.

(56) References Cited

U.S. PATENT DOCUMENTS

2001/0055462 A1*  12/2001  Seibel .......................... 385/147
2005/0182295 A1*   8/2005  Soper et al. .................. 600/117

(Continued)

FOREIGN PATENT DOCUMENTS

JP    2010-162090 A    7/2010
JP    2010-213764 A    9/2010

(Continued)

*Primary Examiner* — John P Leubecker (74) *Attorney, Agent, or Firm* — Scully, Scott, Murphy & Presser, PC (57) ABSTRACT

An endoscope apparatus includes: an insertion portion to be inserted into a living body, an optical fiber that is inserted through the insertion portion and emits light from a light source, a fixing member that holds the optical fiber in the insertion portion in a state where the optical fiber is protruded in a distal end direction of the insertion portion, an actuator that causes the distal end of the optical fiber to swing, and a distal end optical system having an optical characteristic in which a focal point position of the light is behind a distal end of the insertion portion when the optical fiber protruded from the fixing member is shortened by a predetermined length.

9 Claims, 9 Drawing Sheets

(56) References Cited

U.S. PATENT DOCUMENTS

| | | |
|---|---|---|
| 2007/0149851 A1* | 6/2007 | Nakamura et al. ............ 600/129 |
| 2007/0236782 A1* | 10/2007 | Sano ............................. 359/368 |
| 2008/0221388 A1* | 9/2008 | Seibel et al. .................. 600/109 |
| 2010/0125167 A1* | 5/2010 | Sugimoto ..................... 600/109 |
| 2010/0179386 A1 | 7/2010 | Kobayashi |
| 2014/0073950 A1* | 3/2014 | Akui et al. .................... 600/478 |

FOREIGN PATENT DOCUMENTS

| | | |
|---|---|---|
| JP | 2011-019706 A | 2/2011 |
| JP | 2011-156235 A | 8/2011 |

* cited by examiner

| SURFACE NUMBER | r | d | nd | vd |
|---|---|---|---|---|
| OBJECT SURFACE | ∞ | 7.50 | | |
| 1 | ∞ | 1.0 | 1.89019 | 40.76 |
| 2 | −0.5100 | 0.06 | | |
| 3 | 0.4750 | 0.40 | 1.89019 | 40.76 |
| 4 | ∞ | 0.06 | | |
| IMAGE SURFACE | ∞ | | | |

FIG. 5

| LENGTH OF BROKEN PART OF OPTICAL FIBER (mm) | FOCAL POINT POSITION (mm) |
|---|---|
| 0 | 8.184 |
| 1.75 | -0.221 |
| 2.625 | -0.237 |
| 3.5 | -0.245 |

SCANNING ENDOSCOPE APPARATUS

CROSS REFERENCE TO RELATED APPLICATION

This application is a continuation application of PCT/JP2013/075001 filed on Sep. 17, 2013 and claims benefit of Japanese Application No. 2012-226227 filed in Japan on Oct. 11, 2012, the entire contents of which are incorporated herein by this reference.

BACKGROUND OF THE INVENTION

1. Field of the Invention

The present invention relates to an endoscope apparatus and, more particularly, to an endoscope apparatus that acquires image signals through laser light scanning 2. Description of the Related Art As is well-known, electronic endoscopes are used that carry out photoelectric conversion of a subject image by employing an image pickup apparatus including a solid-state image pickup device such as a CCD and CMOS and displays an acquired image on a monitor. In recent years, scanning endoscope apparatuses have been used for displaying a subject image, without employing the technology of the solid-state image pickup device. The scanning endoscope apparatus scans a subject with a distal end of an illumination fiber that guides light from a light source, receives return light from the subject with an optical fiber bundle disposed around the illumination fiber, and generates a subject image by using chronologically detected light intensity signals.

For example, Japanese Patent Application Laid-Open Publication No. 2011-19706 discloses a medical observation system including a scanning medical probe that transmits laser light from a laser light source to a distal end portion of an insertion portion via a single-mode optical fiber and irradiates the subject.

The medical observation system disclosed in Japanese Patent Application Laid-Open Publication No. 2011-19706 has an optical fiber inserted through and fixed in a through hole of an actuator formed with a piezoelectric device or the like and supplies a driving voltage to a plurality of electrodes provided to the actuator in XY-axis direction to cause the optical fiber to vibrate in a predetermined manner and scan the laser light.

Figure 9A:
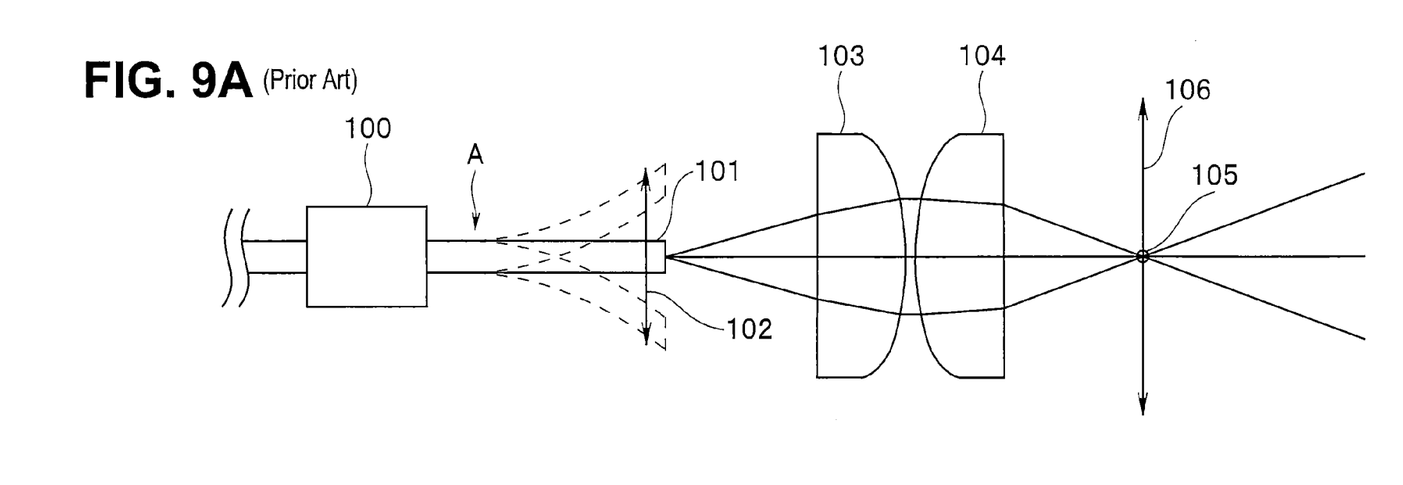
FIG. 9A is a view for illustrating a state of propagation of a laser light in conventional arts.

FIG. 9A is a view for illustrating a state of propagation of a laser light in conventional arts.

As shown in FIG. 9A, a conventional scanning endoscope apparatus drives an actuator 100 to vibrate (double-pointed arrow 102) an optical fiber 101. The laser light emitted from the optical fiber 101 is concentrated, for example, at a focal point 105 by lenses 103, 104 constituting a distal end optical system. The vibration (double-pointed arrow 102) of the optical fiber 101 also causes the focal point 105 to vibrate (double-pointed arrow 106), thereby allowing to scan a living body with the laser light.

Figure 9B:
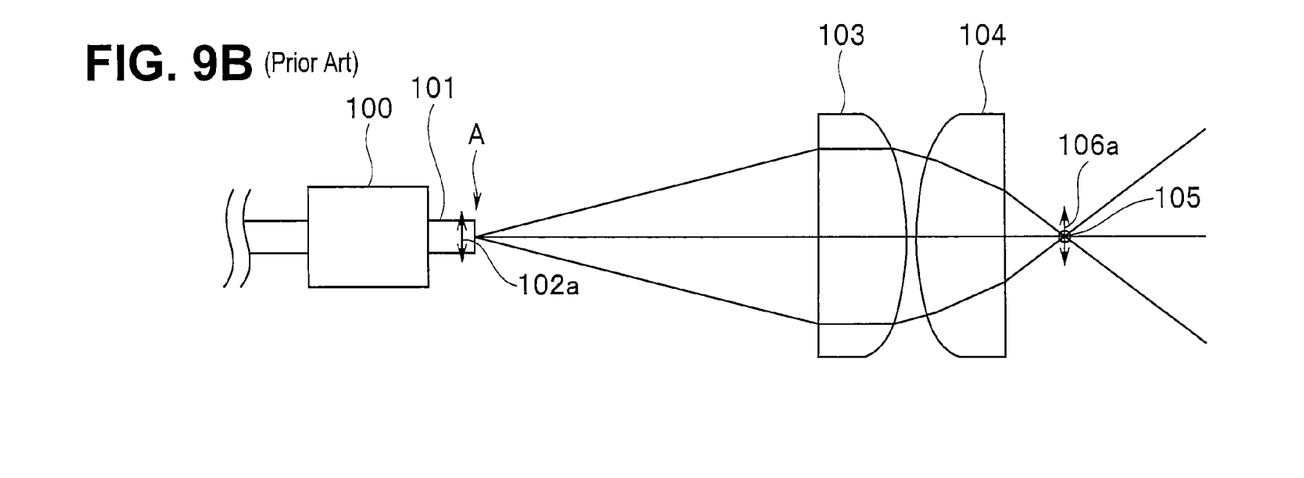
FIG. 9B is a view for illustrating a state of propagation of a laser light when the optical fiber is broken in conventional arts.

FIG. 9B is a view for illustrating a state of propagation of a laser light when the optical fiber is broken in conventional arts. As shown in FIG. 9B, when a part of the optical fiber 101 is broken which is on a distal end side with respect to the actuator 100, almost no amplitude (double-pointed arrow 102a) of the optical fiber 101 can be acquired.

SUMMARY OF THE INVENTION

An endoscope apparatus according to one aspect of the present invention includes: an insertion portion to be inserted into a living body; an optical fiber that is inserted through the insertion portion and emits light from a light source; a fixing member that holds the optical fiber in the insertion portion in a state where the optical fiber is protruded in a distal end direction of the insertion portion; an actuator that is disposed in the insertion portion and causes a distal end of the optical fiber to swing; and an illumination optical system having an optical characteristic in which a focal point position of the light is behind a distal end of the insertion portion when the optical fiber protruded from the fixing member is shortened by a predetermined length.

DETAILED DESCRIPTION OF THE PREFERRED EMBODIMENT

Hereinafter, an embodiment of the present invention will be described with reference to the drawings.

First, the entire configuration of an endoscope apparatus according to one embodiment will be described with reference to FIG. 1.

Figure 1:
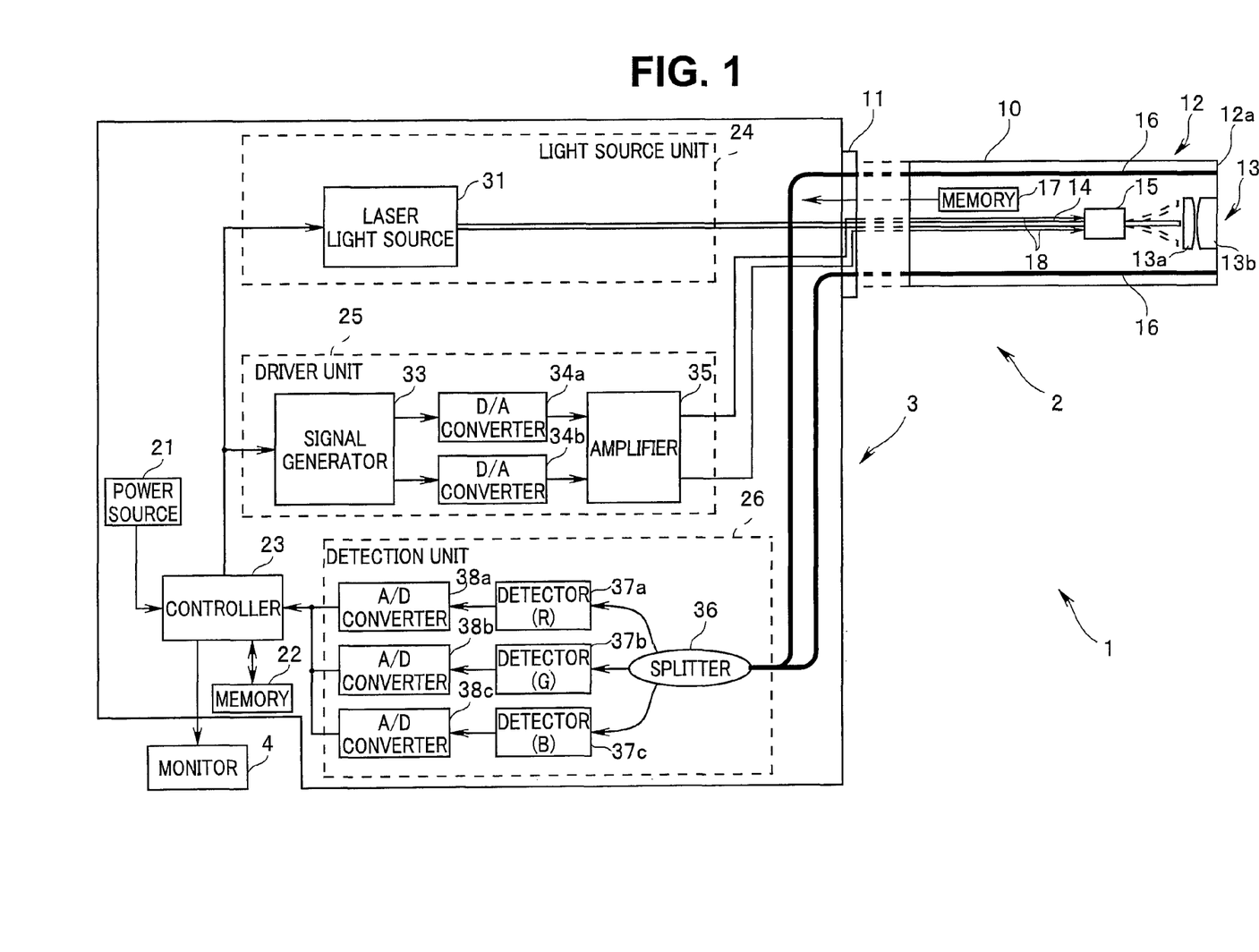
FIG. 1 is a view showing a configuration of an endoscope apparatus according to one embodiment.

FIG. 1 is a view showing the configuration of the endoscope apparatus according to the one embodiment.

As shown in FIG. 1, the endoscope apparatus 1 includes a scanning endoscope 2 that irradiates a subject with laser light (illumination light) while scanning the subject and receives return light from the subject, a main apparatus 3 that is connected to the endoscope 2, and a monitor 4 that displays a subject image acquired by the main apparatus 3.

The endoscope 2 is mainly constituted of a tube body that has a predetermined flexibility and includes an elongated insertion portion 10 to be inserted in a living body. A connector 11 is provided on a proximal end side of the insertion portion 10, and the endoscope 2 is configured to be attachable to and detachable from the main apparatus 3 via the connector 11. A distal end portion 12 is provided on a distal end side of the insertion portion 10.

A distal end optical system 13 constituted of illumination lenses 13a, 13b is provided on a distal end surface 12a of the distal end portion 12. Inside the insertion portion 10 are provided an optical fiber 14 serving as an optical device that is inserted from the proximal end side to the distal end side, guides light from a light source unit 24 described below and irradiates the living body with the laser light, and actuators 15 that are provided on a distal end side of the optical fiber 14 and cause a distal end of the optical fiber 14 to scan in desired directions based on driving signals from a driver unit 25 described below. With this configuration, the subject is irradiated with the laser light emitted from the light source unit 24 and guided by the optical fiber 14.

Also provided inside the insertion portion 10 are detection fibers 16 serving as a light receiving portion inserted through from the proximal end side to the distal end side along an internal circumference of the insertion portion 10 and receives the return light from the subject. Distal end surfaces of the detection fibers 16 are disposed around the distal end optical system 13 on the distal end surface 12a of the distal end portion 12. The detection fibers 16 may be at least two or more fiber bundles. When the endoscope 2 is connected to the main apparatus 3, the detection fibers 16 are connected to a splitter 36 described below.

Inside the insertion portion 10 is also provided a memory 17 storing various information on the endoscope 2. When the endoscope 2 is connected to the main apparatus 3, the memory 17 is connected to a controller 23 described below via a signal cable (not shown), and the various information on the endoscope 2 is read by the controller 23.

On the optical fiber 14, a plurality of conductive wires 18 are evaporated which are made of, for example, a linear metal material, from the connector 11 to the actuators 15 of the distal end portion 12. The actuators 15 are provided at distal ends of the plurality of conductive wires 18. The plurality of conductive wires 18 are connected to an amplifier 35 of the main apparatus 3 when the connector 11 is attached to the main apparatus 3. The plurality of conductive wires 18 constitute a conductive portion that conducts driving signals for driving the actuators 15.

The main apparatus 3 is constituted of a power source 21, a memory 22, the controller 23, the light source unit 24, the driver unit 25, and a detection unit 26.

The light source unit 24 includes a laser light source 31. The driver unit 25 includes a signal generator 33, digital-analog (hereinafter "D/A") converters 34a, 34b, and the amplifier 35.

The detection unit 26 includes the splitter 36, detectors 37a to 37c, and analog-digital (hereinafter "A/D") converters 38a to 38c.

The power source 21 controls supply of power to the controller 23 in response to an operation of a power switch (not shown) and the like. The memory 22 stores control programs and the like for controlling the entirety of the main apparatus 3.

When supplied with power from the power source 21, the controller 23 reads the control programs from the memory 22, controls the light source unit 24 and the driver unit 25 while analyzing the light intensity of the return light from the subject which is detected by the detection unit 26, and controls to cause the monitor 4 to display an acquired subject image.

The laser light source 31 of the light source unit 24 emits laser light (illumination light) in a predetermined wavelength band to the optical fiber 14 on the basis of the control by the controller 23. The optical fiber 14 emits the laser light (illumination light) from the laser light source 31 to an object.

The signal generator 33 of the driver unit 25 outputs the driving signals to cause the distal end of the optical fiber 14 to scan (scan driving) in a desired direction, for example, spirally, on the basis of the control by the controller 23. Specifically, the signal generator 33 outputs, to the D/A converter 34a, the driving signal that drives the distal end of the optical fiber 14 in a right-and-left direction (X-axis direction) with respect to the insertion axis of the insertion portion 10, and outputs to the D/A converter 34b the driving signal that drives the distal end of the optical fiber 14 in an up-and-down direction (Y-axis direction) with respect to the insertion axis of the insertion portion 10.

The D/A converters 34a, 34b convert the respective inputted driving signals from digital signals to analog signals and output the analog signals to the amplifier 35. The amplifier 35 amplifies the inputted driving signals and outputs the amplified driving signals to the actuators 15. The driving signals outputted from the amplifier 35 are supplied to the actuators 15 via the plurality of conductive wires 18 evaporated onto the optical fiber 14.

The actuators 15 serving as a drive portion cause the distal end (free end) of the optical fiber 14 to swing and spirally scan the subject on the basis of the driving signal from the amplifier 35. Consequently, the subject is spirally and sequentially irradiated with the light emitted from the laser light source 31 of the light source unit 24 to the optical fiber 14.

The detection fibers 16 receive the return light reflected in a surface region of the subject and guide the received return light to the splitter 36.

The splitter 36 is a dichroic mirror, for example, and splits the return light in accordance with predetermined wavelength bands. Specifically, the splitter 36 splits the return light guided by the detection fibers 16 into return lights in the R, G and B wavelength bands, and outputs the return lights to the detectors 37a, 37b and 37c, respectively.

The detectors 37a, 37b and 37c detect the respective light intensities of the return lights in the R, G and B wavelength bands. The signals of the light intensities detected by the detectors 37a, 37b and 37c are outputted to the A/D converters 38a, 38b and 38c, respectively.

The A/D converters 38a to 38c convert the signals of the light intensities outputted respectively from the detectors 37a to 37c from the analog signals to the digital signals and output the converted digital signals to the controller 23.

The controller 23 performs a predetermined image processing on the digital signals from the A/D converters 38a to 38c to generate a subject image, and displays the subject image on the monitor 4.

A detailed configuration of the distal end portion 12 of the insertion portion 10 will be described here with reference to FIGS. 2 and 3.

Figure 2:
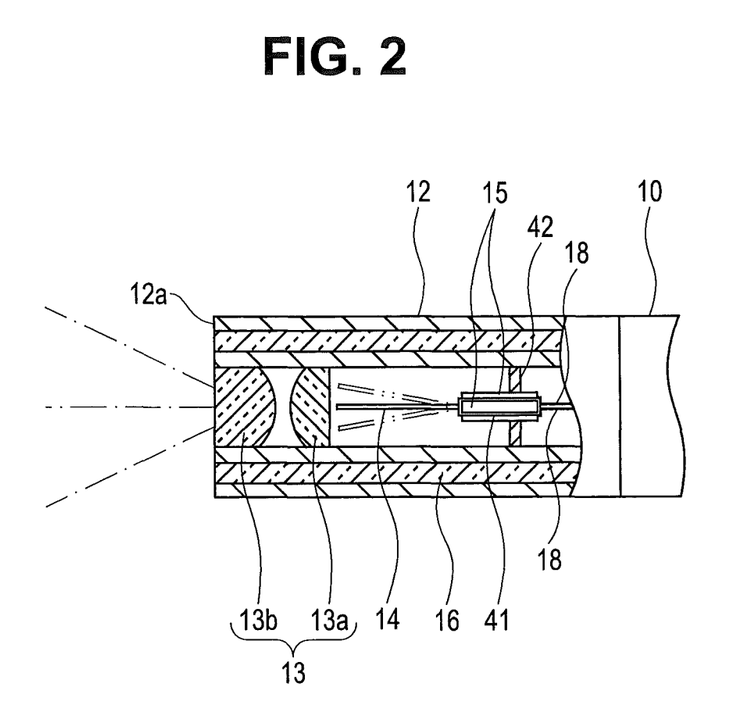
FIG. 2 is a sectional view for illustrating a configuration of a distal end portion 12 of an insertion portion 10.
Figure 3:
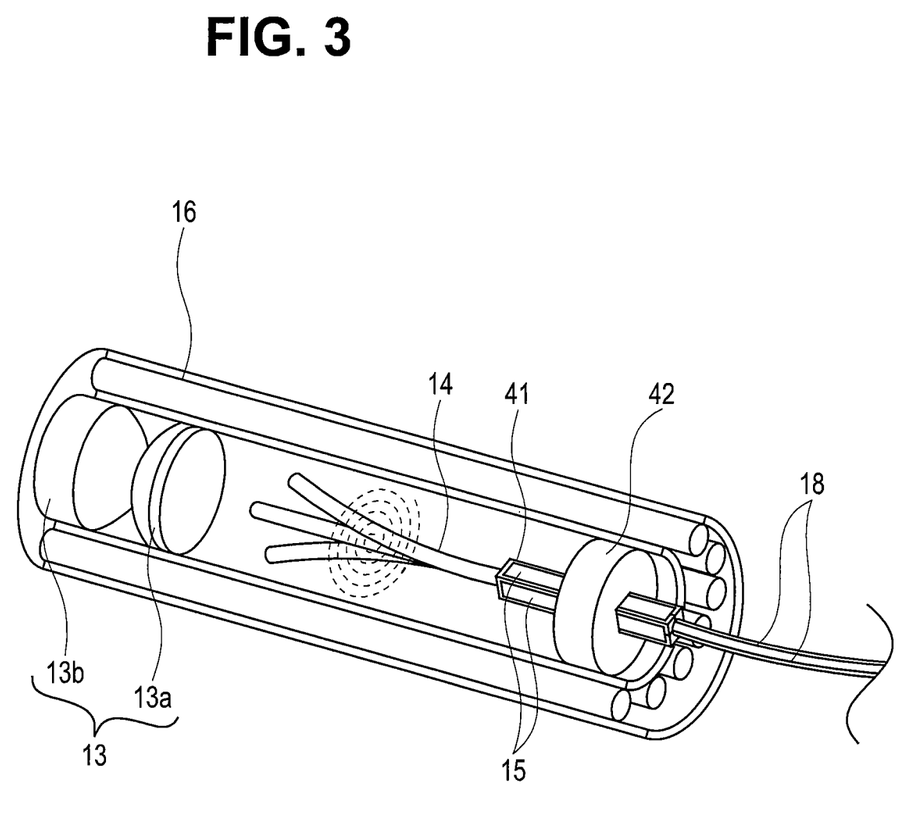
FIG. 3 is a perspective view for illustrating the configuration of the distal end portion 12 of the insertion portion 10.

FIG. 2 is a sectional view for illustrating the configuration of the distal end portion 12 of the insertion portion 10, and FIG. 3 is a perspective view for illustrating the configuration of the distal end portion 12 of the insertion portion 10.

As shown in FIGS. 2 and 3, the distal end portion 12 of the insertion portion 10 includes a ferrule 41 serving as a junction member which is disposed between the optical fiber 14 and the actuators 15. The ferrule 41 is a member used in the field of optical communications, and is made of a material such as zirconia (ceramic) and nickel to facilitate a highly accurate (for example, ±1 μm) center-hole drilling for an outer diameter (for example, 125 μm) of the optical fiber 14. At the substantial center of the ferrule 41 is provided a through hole in accordance with the diameter of the optical fiber 14, that is, the ferrule 41 is subjected to center-hole drilling, and the optical fiber 14 is fixed in the through hole with an adhesive or the like.

The ferrule 41 has a quadrangular prism shape, and the actuators 15 are disposed on respective side surfaces of the ferrule 41 having the quadrangular prism shape. The actuators 15, the ferrule 41, and the optical fiber 14 are fixed at the substantial center of the distal end portion 12 with a fixing member 42 in the distal end portion 12. The ferrule 41 thus has the actuators 15 adhered thereon and grasps an outer circumference of the optical fiber 14.

The plurality of conductive wires 18 are connected to the actuators 15 disposed on the respective side surfaces of the ferrule 41, and thereby the driving signals from the driver unit 25 are supplied to the actuators 15 via the conductive wires 18. The actuators 15 are piezoelectric elements (piezoelectric devices), for example, and expand and contract in response to the driving signals from the driver unit 25, thereby allowing to spirally scan the subject with the distal end of the optical fiber 14. The laser light emitted from the optical fiber 14 is then concentrated in the distal end optical system 13 and the subject is irradiated with the laser light.

The distal end optical system 13 (illumination optical system) is disposed to face the optical fiber 14 and constituted of the illumination lens 13a which is a plano-convex lens and the illumination lens 13b which is a convex-plano lens. In the distal end optical system 13, the illumination lens 13a which is the plano-convex lens and the illumination lens 13b which is the convex-plano lens are disposed in this order from a side of the laser light source 31.

The distal end optical system 13, which will be detailed later with reference to FIGS. 5 to 8, has an optical characteristic such that the focal point of the laser light is within the distal end optical system 13 when the optical fiber 14 protruded from the distal end of the ferrule 41 by a predetermined length is broken, for example, and becomes shorter than a predetermined length. Note that, the distal end optical system 13, which is constituted of two illumination lenses 13a, 13b, may be constituted of three or more illumination lenses, for example.

Figure 4:
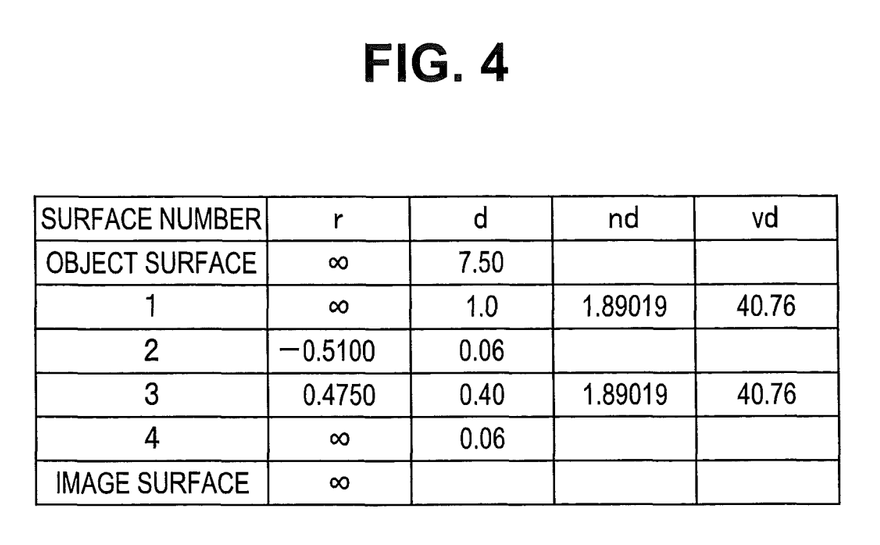
FIG. 4 is a view showing lens data of a distal end optical system 13 constituted of illumination lenses 13a, 13b.

Lens data of the distal end optical system 13 constituted of the illumination lenses 13a, 13b are shown in FIG. 4. FIG. 4 shows lens data of the distal end optical system 13 constituted of the illumination lenses 13a, 13b.

Reference signs used in FIG. 4 are as follows.
r: radius of curvature (mm)
d: spacing (mm)
nd: refractive index
vd: Abbe number Next, the relation between the length of the broken part of the optical fiber 14 and the focal point position of the laser light will be described with reference to FIGS. 5 to 8.

Figure 5:
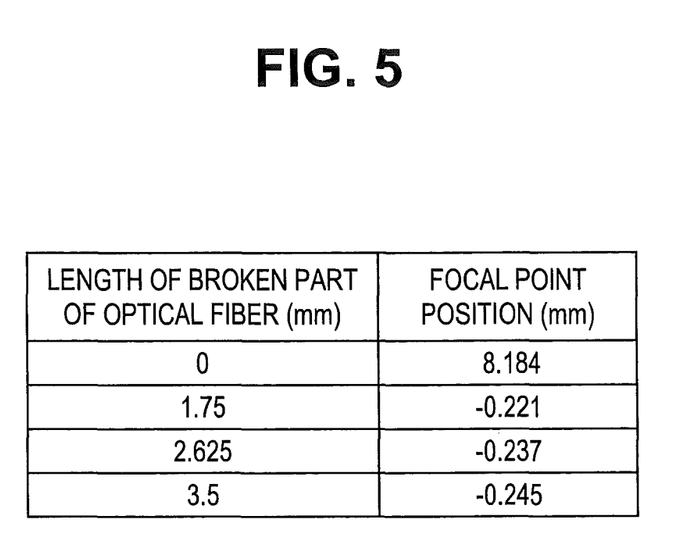
FIG. 5 is a view for illustrating the relation between a length of a broken part of an optical fiber 14 and a focal point position of laser light.
Figure 6:
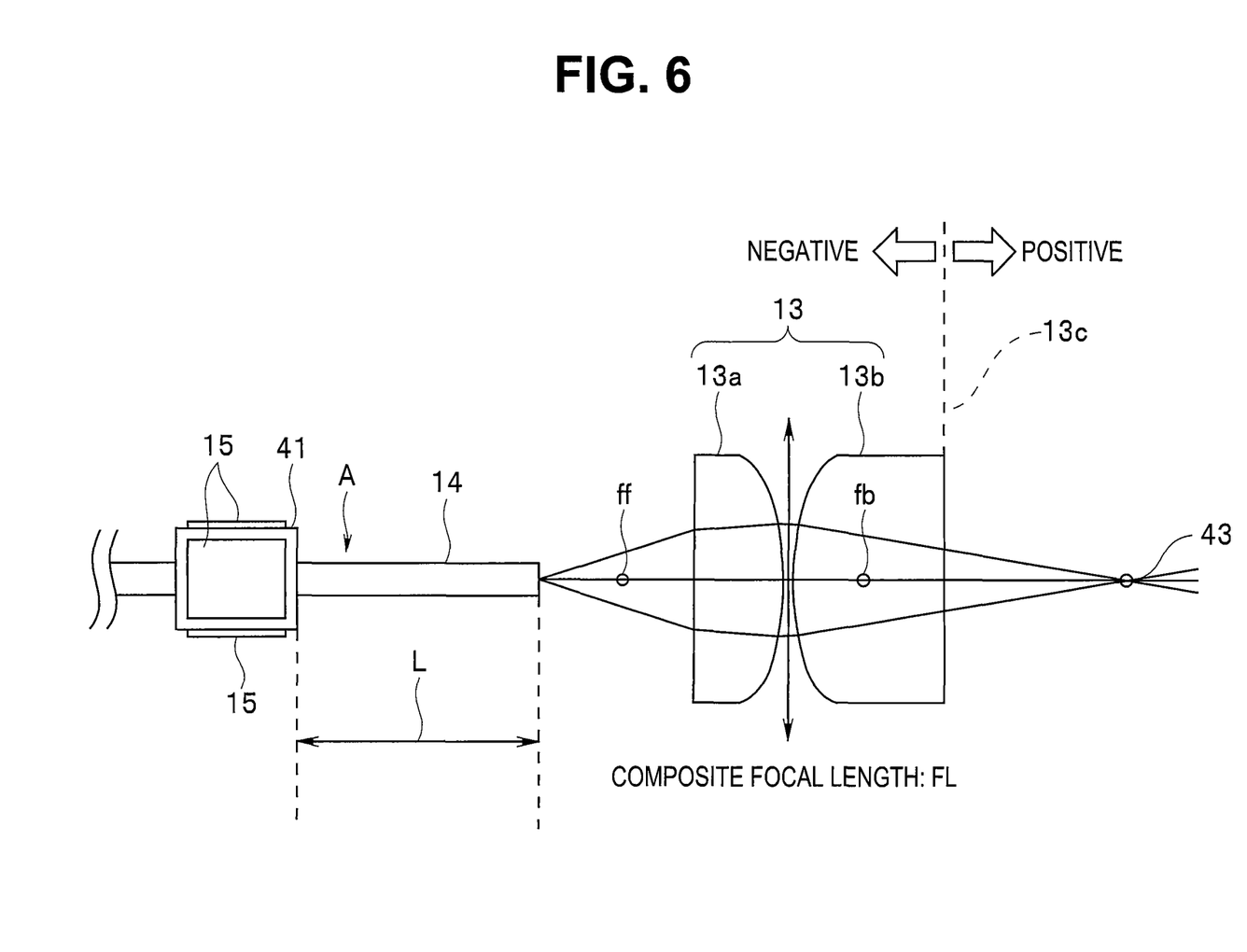
FIG. 6 is a view for illustrating a state of propagation of the laser light when the length of the broken part of the optical fiber 14 is 0 mm.
Figure 7:
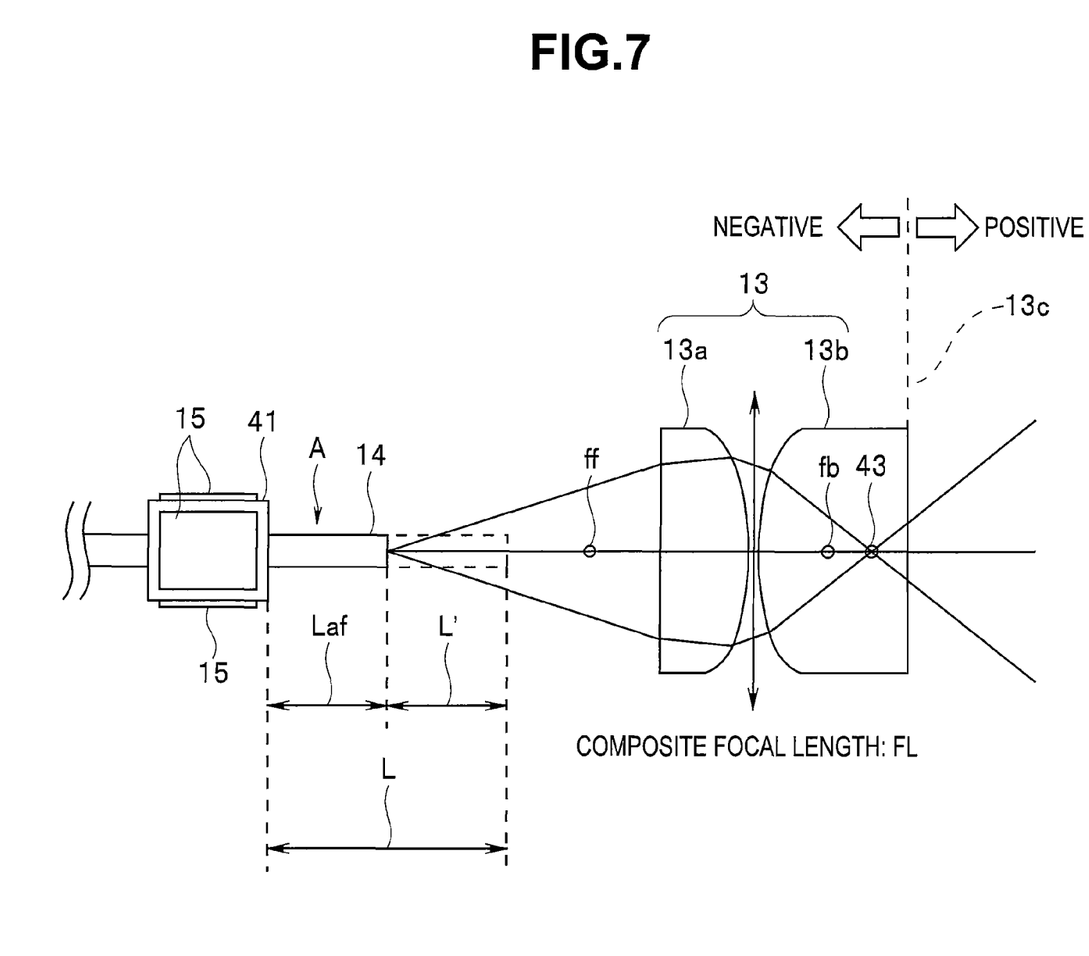
FIG. 7 is a view for illustrating a state of propagation of the laser light when the length of the broken part of the optical fiber 14 is 1.75 mm.
Figure 8:
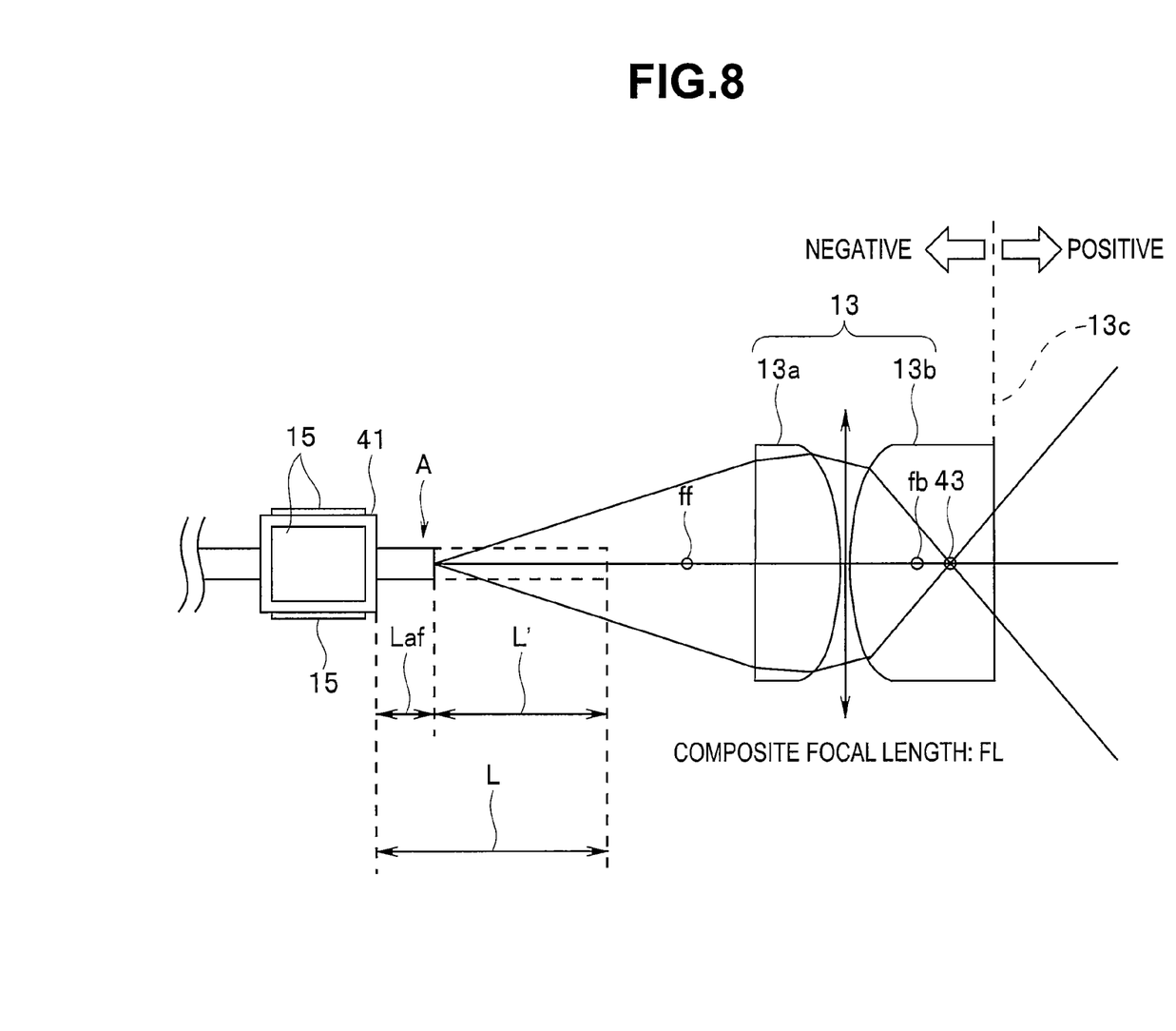
FIG. 8 is a view for illustrating a state of propagation of the laser light when the length of the broken part of the optical fiber 14 is 2.625 mm.

FIG. 5 is a view for illustrating the relation between the length of the broken part of the optical fiber 14 and the focal point position of the laser light. FIG. 6 is a view for illustrating a state of propagation of the laser light when the length of the broken part of optical fiber 14 is 0 mm. FIG. 7 is a view for illustrating a state of propagation of the laser light when the length of the broken part of the optical fiber 14 is 1.75 mm. FIG. 8 is a view for illustrating a state of propagation of the laser light when the length of the broken part of the optical fiber 14 is 2.625 mm. In FIGS. 6 to 8, the same constituent elements are denoted with the same reference signs.

FIG. 5 shows the relation between the length L' of the broken part of the optical fiber 14 (see FIGS. 7 and 8) and the focal point position 43 of the laser light (see FIGS. 6 to 8). The focal point position 43 is defined as being positive when being in front of a distal end portion 13c (on a side of the living body and the right side in FIG. 6), and defined as being negative when being behind the distal end portion 13c (on a side of the optical fiber 14 and the left side in FIG. 6), with the distal end portion 13c of the illumination lens 13b on the distal end side in FIG. 6 being used as a reference. That is, when the length L' of the broken part of optical fiber 14 is 0 mm, the focal point position 43 is in front of the distal end portion 13c of the illumination lens 13b, and when the length L' of the broken part of the optical fiber 14 is greater than 1.75 mm, the focal point position 43 is behind the distal end portion 13c of the illumination lens 13b.

As shown in FIG. 6, the optical fiber 14 is protruded from the ferrule 41 in the direction toward the distal end optical system 13 by a predetermined length, and the length of the protrusion of the optical fiber 14 is represented with L. According to the present embodiment, the length L of the optical fiber 14 protruded from the ferrule 41 in the direction toward the distal end optical system 13 is defined 3.5 mm.

In FIG. 6, the reference sign A represents the position where stresses on the optical fiber 14 concentrate, ff represents a front focal position of the distal end optical system 13, fb represents a back focal position, and FL represents a composite focal position. In the present embodiment, the composite focal position FL of the distal end optical system 13 is defined to be 0.15 mm. As shown in FIG. 6, when the length L' of the broken part of the optical fiber 14 is 0 mm (when the optical fiber 14 has no broken part), the laser light emitted from the optical fiber 14 is concentrated at the focal point position 43 in front of the distal end portion 13c of the illumination lens 13b.

When the length L' of the broken part of optical fiber 14 is 1.75 mm, the focal point position 43 is behind the distal end portion 13c of the illumination lens 13b, and the laser light is concentrated within the distal end optical system 13. In this case, since a divergent light is emitted from the distal end optical system 13, the laser light with which the living body is irradiated can have a value equal to or smaller than a prescribed value.

In the case where the optical fiber 14 is broken and left, the distal end optical system 13 can concentrate the laser light within the distal end optical system 13 by satisfying the following expressions 1 and 2.

$$fb<0 \quad \text{(expression 1)}$$

$$0<Laf/FL<11.67 \quad \text{(expression 2)}$$

Here, Laf represents the length of the optical fiber 14 protruded from the distal end of the ferrule 41 (that is, the length of the optical fiber 14 that is broken and left).

Note that the expression 1 shows that the back focal position fb of the distal end optical system 13 is behind the distal end portion 13c of the illumination lens 13b, that is, being negative.

Similarly, when the length L' of the broken part of optical fiber 14 is 2.625 mm (when the length Laf of the optical fiber 14 that is broken and left is 0.875 mm), conditions of the expressions 1 and 2 are satisfied, and the laser light is concentrated within the distal end optical system 13, as shown in FIG. 8. The divergent light is thus emitted from the distal end optical system 13 and the laser light with which the living body is irradiated can have a value equal to or smaller than the prescribed value.

Note that the present invention is not limited to the distal end optical system 13 as described above in the present embodiment, wherein the focal point position 43 of the laser light is within the distal end optical system 13 when the length L' of the broken part of optical fiber 14 is 1.75 mm or longer. The present embodiment merely describes an example in which the length L' of the broken part of the optical fiber is 1.75 mm or longer in view that the optical fiber 14 is usually liable to break in the vicinity of the position A where stresses concentrate, which is close to the ferrule 41. For example, a distal end optical system may be used wherein the focal point position 43 is within the distal end optical system 13 when the length L' of the broken part of the optical fiber 14 is not smaller than 1.0 mm or not smaller than 0.5 mm.

As described above, the endoscope apparatus 1 is designed to employ the distal end optical system 13 wherein the focal point position 43 of the laser light is within the distal end optical system 13 when the optical fiber 14 protruded from the distal end of the ferrule 41 is broken. As a result, when the optical fiber 14 protruded from the distal end of the ferrule 41 is broken, the living body is irradiated with the divergent light from the distal end optical system 13. The living body is thus prevented from being irradiated with a prescribed or more quantity of laser light.

The endoscope apparatus according to the present embodiment thus allows to ensure the safety of the subject concerning the quantity of laser light even when the optical fiber is broken.

The present invention is not limited to the embodiment and modifications described above, and various changes or modifications can be made within the range not departing from the gist of the present invention.

What is claimed is:

1. A scanning endoscope apparatus comprising:
an insertion portion to be inserted into a living body;
an optical fiber that is inserted through the insertion portion and emits light from a light source;
a fixing member that holds the optical fiber in the insertion portion in a state where the optical fiber is protruded in a distal end direction of the insertion portion;
an actuator that is disposed in the insertion portion and causes a distal end of the optical fiber to swing; and
an illumination optical system disposed in the insertion portion so as to face a distal end of the optical fiber along the distal end direction, wherein
the illumination optical system has an optical characteristic in which a focal point position of the light changes from a position on a more distal side than a distal end of the illumination optical system to a position on a more proximal side than the distal end of the illumination optical system when the optical fiber protruded from the fixing member is shortened by a predetermined length.

2. The scanning endoscope apparatus according to claim 1, further comprising
a ferrule on which the actuator is adhered and which grasps an outer circumference of the optical fiber in a state where the optical fiber is protruded in the distal end direction of the insertion portion, wherein
the illumination optical system has an optical characteristic in which the focal point position of the light changes from a position on a more distal side than the distal end of the illumination optical system to a position on the more proximal side than the distal end of the illumination optical system when the optical fiber protruded from a distal end of the ferrule is shortened by a predetermined length.

3. The scanning endoscope apparatus according to claim 2, wherein the illumination optical system satisfies the following conditional expressions (1) and (2):

$$fb<0 \quad (1); \text{and}$$

$$0<Laf/FL<11.67 \quad (2),$$

where fb represents a back focal position of the illumination optical system, Laf represents a distance of protrusion of the optical fiber from the distal end of the ferrule when the optical fiber becomes shorter than the predetermined length, and FL represents a composite focal length of the illumination optical system.

4. The scanning endoscope apparatus according to claim 1, wherein the illumination optical system includes a plano-convex lens and a convex-plano lens.

5. The scanning endoscope apparatus according to claim 4, wherein the illumination optical system includes the plano-convex lens and the convex-plano lens disposed in this order from a side of the light source.

6. The scanning endoscope apparatus according to claim 1, wherein the optical fiber emits laser light as the light from the light source.

7. A scanning endoscope apparatus comprising:
an insertion portion to be inserted into a living body;
an optical fiber that is inserted through the insertion portion and emits light from a light source;
a fixing member that holds the optical fiber in the insertion portion in a state where the optical fiber is protruded in a distal end direction of the insertion portion;
an actuator that is disposed in the insertion portion and causes a distal end of the optical fiber to swing;
a ferrule on which the actuator is adhered and which grasps an outer circumference of the optical fiber in a state where the optical fiber is protruded in the distal end direction of the insertion portion; and
an illumination optical system which has an optical characteristic in which the focal point position of the light is proximal to a distal end of the insertion portion when the optical fiber protruded from a distal end of the ferrule is shortened by a predetermined length and which satisfies the following conditional expressions (1) and (2):

$$fb<0 \quad (1); \text{and}$$

$$0<Laf/FL<11.67 \quad (2),$$

where fb represents a back focal position of the illumination optical system, Laf represents a distance of protrusion of the optical fiber from the distal end of the ferrule when the optical fiber becomes shorter than the predetermined length, and FL represents a composite focal length of the illumination optical system.

8. The scanning endoscope apparatus according to claim 7, wherein the illumination optical system includes a plano-convex lens and a convex-plano lens.

9. The scanning endoscope apparatus according to claim 8, wherein the illumination optical system includes the plano-convex lens and the convex-plano lens disposed in this order from a side of the light source.

* * * * *